United States Patent [19]

Nagabhushan et al.

[11] Patent Number: 4,636,383

[45] Date of Patent: Jan. 13, 1987

[54] INTERFERON-CYCLARADINE COMBINATION

[75] Inventors: Tattanahali L. Nagabhushan, Parsippany; George H. Miller, Montville, both of N.J.; Jerome Schwartz, New York, N.Y.; Michael R. Ostrander, Glen Ridge, N.J.

[73] Assignee: Schering Corporation, Kenilworth, N.J.

[21] Appl. No.: 645,370

[22] Filed: Aug. 29, 1984

[51] Int. Cl.[4] ........................ A61K 45/02; C12P 21/00
[52] U.S. Cl. .......................................... 424/85; 435/68
[58] Field of Search ............................ 424/85; 435/68; 544/277

[56] References Cited

U.S. PATENT DOCUMENTS 4,383,114   5/1983   Vince ................................ 544/277
4,461,757   7/1984   Ogilvie ................................ 424/85
4,462,986   7/1984   Smith ................................ 424/85

OTHER PUBLICATIONS

Chemical Abstracts, vol. 94, Abst. No. 185483s, 1981.

*Primary Examiner*—Blondel Hazel
*Attorney, Agent, or Firm*—Anita W. Magatti; Gerald S. Rosen

[57] ABSTRACT

Treatment of viral infections with combinations of cyclaradine and interferon and compositions and kits used therein are disclosed.

18 Claims, 2 Drawing Figures

INTERFERON-CYCLARADINE COMBINATION

The present invention relates to the treatment of viral infections with a combination of the synthetic antiviral agent cycladarine and an interferon, which interferon is a protein occurring naturally in vivo and/or produced in vitro, and to antiviral compositions comprising cyclaradine and an interferon. More particularly, this invention concerns the treatment of viral infections with cyclaradine or its prodrug esters and the interferon designated alpha interferon. In its most preferred aspect, this invention relates to the treatment of infections caused by Herpes simplex virus in humans by administering a combination of alpha interferon and (+)-cyclaradine or its lower alkoxyalkanoate esters.

BACKGROUND OF THE INVENTION

Herpes simplex viral (HSV) infections are caused by two major types of the virus, Type I, which is an oral type and is usually the cause of Herpes labialis, and Type II, which is usually the cause of Herpes genitalis. Both types of virus are common worldwide, and present serious medical and emotional problems to those infected.

HSV infections have been treated with a combination of alpha interferon and the antiviral agent acyclovir (ACV), but cannot be effectively treated with this combination if this treatment is delayed 24 hours after exposure. The combination of interferon and cyclaradine of this invention accomplishes a reduction in virus titer with a low interferon concentration, and is effective even when initiation of treatment is delayed by 24 hours or more after exposure.

The present invention contemplates the combination of cyclaradine with all interferon types, i.e., natural or recombinant alpha (leucocyte), beta (fibroblast) or gamma (immune) interferon, but alpha interferons are preferred. As used herein, the term "alpha interferon" means a natural or recombinant interferon exhibiting biological properties similar to those of human leucocyte interferon. It should be noted that a number of alpha interferon species are known, usually designated by a numeral after the Greek letter, and all are contemplated for use in this invention. Also included within the scope of this invention are the socalled alpha hybrid interferons wherein fragments of two or more native alpha interferon species are joined (See for instance, EP No. 51873). Preferred forms of alpha interferon for use in the formulations of the present invention are alpha-1 and alpha-2 interferon. Particularly preferred for use in the formulations of the present invention is alpha-2 interferon. Alpha-2 interferon may be prepared by recombinant-DNA methods, for example those disclosed by Nagata et al., Nature, Vol. 284, pages 316–320 (1980).

The antiviral agent cyclaradine (i.e. [1R-(1α,2β,3β,5β)]-3-(6-amino-9H-purin-9-yl)-5-(hydroxymethyl)-1,2-cyclopentanediol) and its preparation are described in U.S. Pat. Nos. 4,383,114, 4,268,672 and 4,138,562. Prodrug alkoxyalkanoate esters (e.g. the 5'-methoxyacetate ester) of cyclaradine are described in U.S. Pat. No. 4,362,729, with the 5'-ethoxypropionate ester and the pharmaceutically acceptable salts thereof being specifically disclosed in a patent application of Robert Vince titled "(3-Ethoxypropionate) Esters of Cyclaradine" filed July 30, 1984. As used herein, "cyclaradine" includes (+)- or (+)- cyclaradine and lower alkoxyalkanoate esters thereof, although (+)-cyclaradine or its esters is preferred.

SUMMARY OF THE INVENTION

Cyclaradine and its lower alkoxyalkanoate esters are known antiviral agents useful in the treatment of HSV. Interferons (INF), particularly alpha interferon, are known antiviral agents active against HSV although they are somewhat less effective against HSV relative to other viruses and are generally used prophylactically against HSV. However, we have found that treatment of HSV infections with a combination of cyclaradine and interferon is more effective than treatment with either agent alone. Furthermore, the combination may be administered simultaneously or sequentially, i.e., the cyclaradine and interferon may be administered together, cyclaradine may be administered first, or interferon may be administered first.

In this invention, INF and cyclaradine may be administered as pharmaceutical compositions which may be administered topically, parenterally, or orally. Preferably, cyclaradine or a prodrug thereof will be administered orally and IFN will be administered topically or parenterally. Oral and parenteral cyclaradine compositions are administered in a dosage range of 1 to 100 mg/kg body weight per day, with 10 to 40 mg/kg per day being preferred. Topical cyclaradine compositions are administered in a dosage range of 1–10% by weight of the formulation (e.g. 10–100 mg/g) preferably in a range of 1–5% by weight. Topical IFN compositions are administered in a dosage range of $10^5$ to $10^8$ International Units (I.U.) of IFN per day with $10^6$ to $10^7$ I.U./day being preferred. Parenteral IFN compositions are administered in a dosage range of $10^5$ to $5 \times 10^7$ I.U./day with $3 \times 10^6$ to $10^7$ I.U./day being preferred.

Typical oral cyclaradine compositions contain 50–500 mg cyclaradine or an equivalent amount of prodrug ester per unit dosage form. Parenteral cyclaradine compositions typically contain 50 to 200 mg cyclaradine per ml. Typical IFN compositions for topical use contain $5 \times 10^5$ to $10^7$ I.U. per gram of topical vehicle. Typical parenteral IFN compositions contain $2.5 \times 10^4$ to $5 \times 10^7$ I.U./ml, preferably $1.5 \times 10^6$ to $10^7$ I.U./ml. Cyclaradine and IFN may be administered separately or in the same composition, wherein the dosage range for each component is the same as for separate administration.

The specific activity of the IFN used in the formulations of the present invention should be at least $1 \times 10^8$ I.U. ± 50%/mgP total protein. Specific activity may be determined by measuring the antiviral activity as compared to the NIH reference standard and by measuring the total protein content using standard methods (e.g. the Lowry Method).

Figure 1:
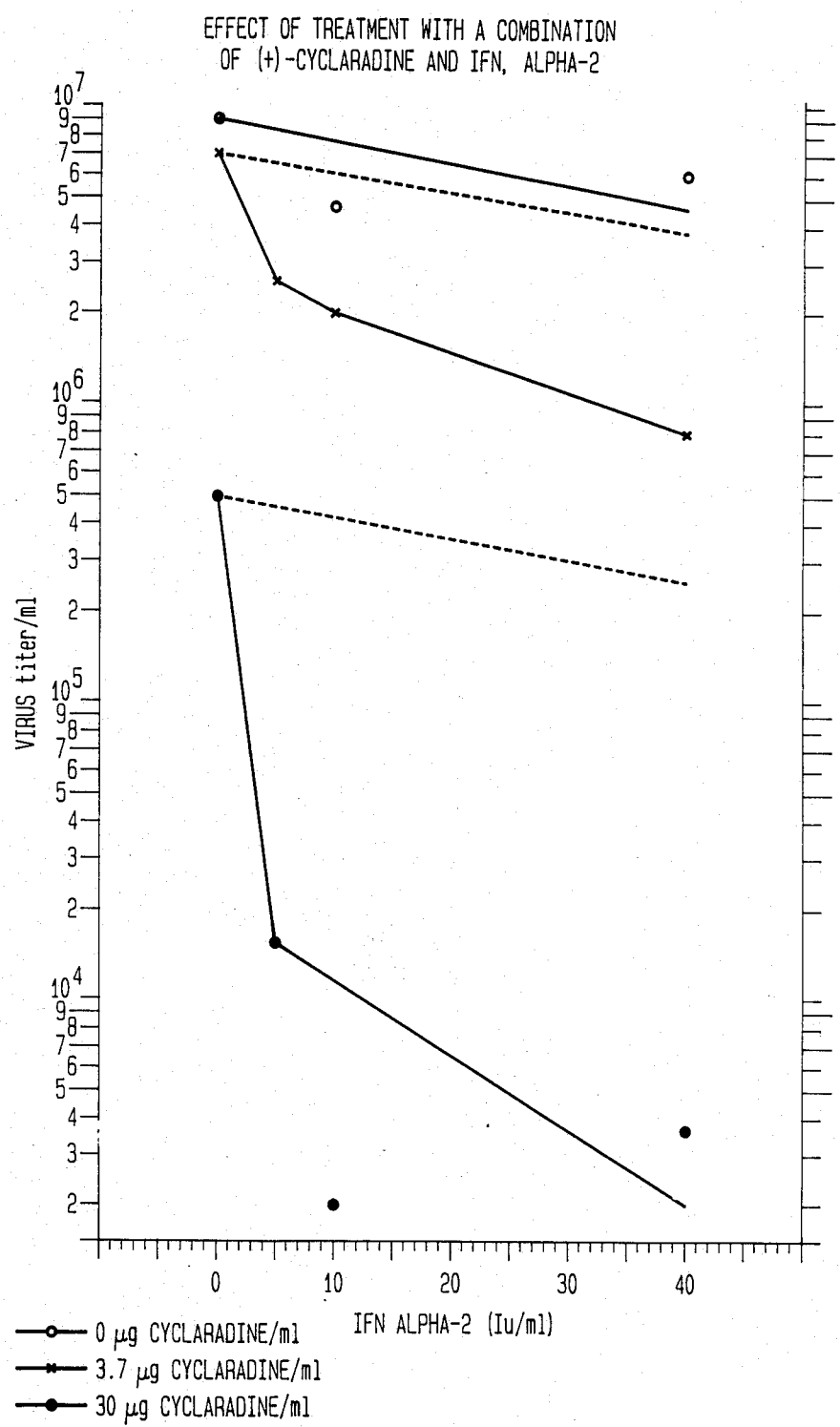
FIG. 1 is a graph showing Virus Titer/ml vs. Concentration of Antiviral Agent.

The combination of IFN and (+)-cyclaradine has been shown to be effective in vitro in the treatment of Herpes simplex virus, and moreover, the observed protection against Herpes simplex demonstrated by the combination exceeds the additive expected protection at the concentrations tested. This result is shown in FIG. 1 wherein a graph of the virus titer/ml versus the concentrations of the combination and the individual agents alone in vitro shows a decrease in actual virus titer of the combination over the expected results. The term "virus titer" refers to the amount of virus per unit volume, i.e., the number of plaque-forming units (infectious units) per ml.

Figure 2:
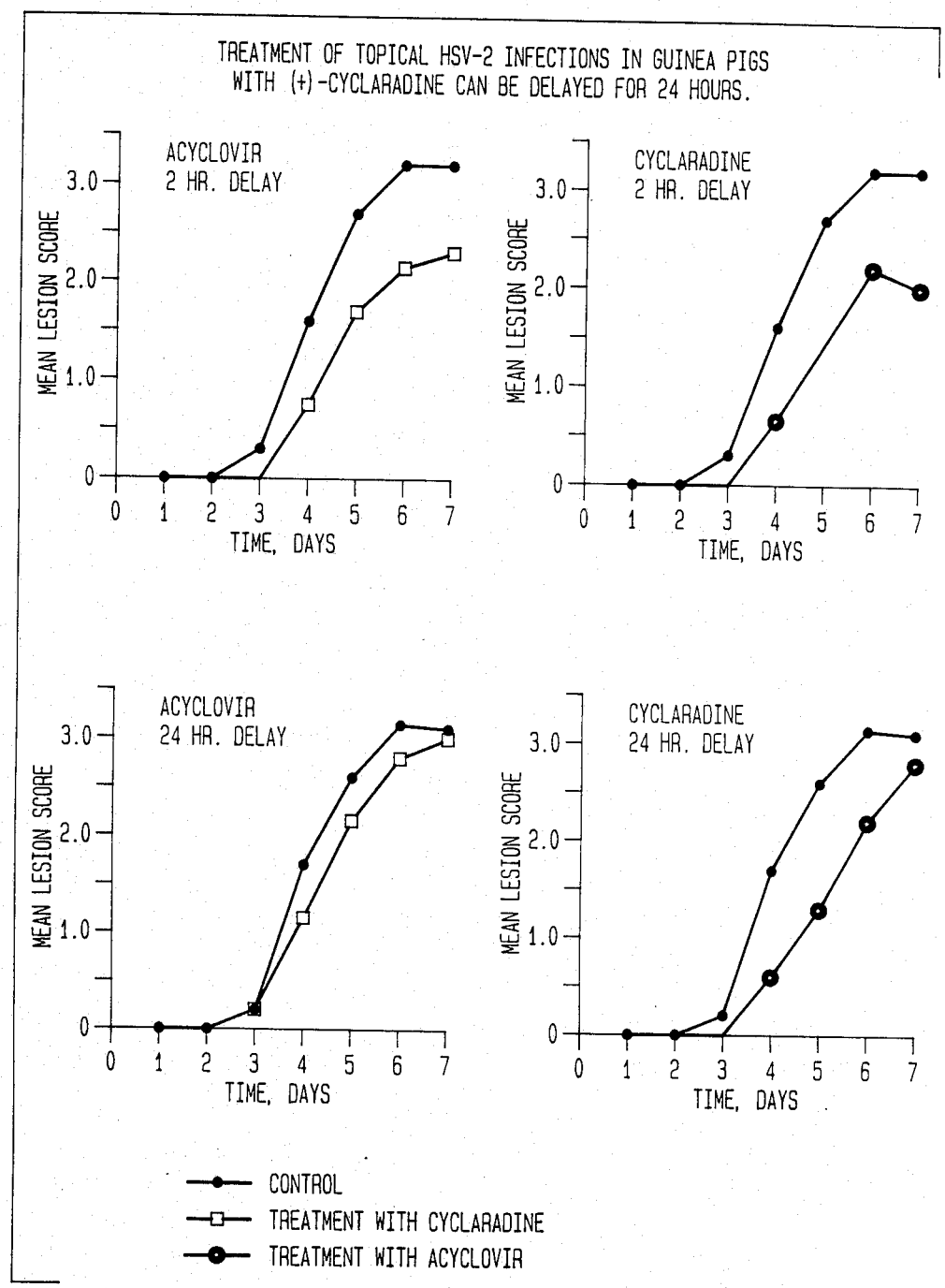
FIG. 2 is a graph showing Mean Lesion Score vs. Time in Days.

An advantage of our combination over ACV alone or in combination with IFN is that cycladrine is active against HSV in the guinea pig vaginal infection model even if initiation of treatment is delayed until 24 hours after infection, whereas ACV is not effective under those conditions. The guinea pig model was used because of its similarity to the human disease and because it is widely accepted as a predictor of the clinical efficacy of ACV. These results are shown in FIG. 2, wherein graphs of mean lesion score vs. time in days for guinea pigs treated with ACV and cycladrine 2-hours and 24-hours post infection indicate that ACV is ineffective after a 24-hour delay in treatment, while cycladrine produces similar reductions in lesions when administered after 2 or after 24 hours. The term "mean lesion score" refers to a measure of lesion development based on the incidence of lesions scored on a scale of 0.5 to 4 (varying from redness and swelling to large ulcers and maceration) and the healing of lesions based on a scale of 3.5 to 0 (with the criteria being the reverse of that above).

Pharmaceutical compositions comprising the combination of this invention may be prepared from standard ingredients using standard techniques. For example, topical compositions include standard liquid formulations, e.g. distilled water or saline solutions, creams and ointments, e.g. oil-in water or water-in-oil emulsions, and other physiologically acceptable carriers such as gelatin, vegetable oils, polyalkylene glycol or alcohol, and aerosols. Injectable formulations use aqueous physiologically acceptable carriers, e.g. distilled water, and preferably contain a compatible buffer system selected to maintain the pH in the desired range of 6.5 to 8, preferably about 7.0 to 7.4. A typical buffer system is a combination of sodium dibasic phosphate and sodium monobasic phosphate.

Oral compositions include tablets, capsules, syrups, elixirs and suspensions. The typical acceptable pharmaceutical carriers for use in the oral formulations described above are exemplified by: sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinylpyrrolidone, polyvinyl alcohol; stearic acid; alkaline earth metal stearates such as magnesium stearate and calcium stearate, stearic acid, vegetable oils such as peanut oil, cottonseed oil, sesame oil, olive oil and corn oil; non-ionic, cationic and anionic sufactants; ethylene glycol polymers; beta-cyclodextrin; fatty alcohols and hydrolyzed cereal solids; as well as other non-toxic compatible filters, binders, disintegrants, buffers, antioxidants, lubricants, flavoring agents, and the like commonly used in pharmaceutical formulations.

In addition to the pharmaceutical carrier and active drugs, the contemplated formulations may also contain preservatives, e.g. glycerine, or stabilizers, e.g. bovine serum albumin (BSA).

Compositions of this invention may be administered one or more times daily, with cycladrine generally administered 1 to 5 times and preferably 3 to 4 times daily, and IFN generally administered 1 to 4 times, preferably 1 to 2 times daily. The combination is usually administered for a period of from 1 to 14, preferably 1 to 7 days. The exact dosage to be administered is based upon the judgment of the clinician, and is dependent upon such factors as the weight and condition of the individual. Examples of compositions are as follows:

Cycladrine compositions:

| Capsules: | Concentration | |
|---|---|---|
| | 50 mg/capsule | 150 mg/capsule |
| 1. Cycladrine | 50 mg | 150 mg |
| 2. Lactose USP | 106 | 73 |
| 3. Corn Starch, Food Grade | 40 | 70 |
| 4. Magnesium Stearate | 4 | 2 |

Blend the ingredients and fill into hard gelatine capsules.

| Oral liquid: | Concentration mg/ml |
|---|---|
| 1. Cycladrine | 50 |
| 2. Sucrose | 800 |
| 3. Glycerin | 0.4 |
| 4. Coloring agent | |
| 5. Flavoring agent | |
| 6. Water | q.s. 1 ml. |

Combine the ingredients using standard techniques.

Interferon Compositions:

| Cream | Concentration |
|---|---|
| 1. Alpha interferon | $10^6$ I.U. |
| 2. Propylene Glycol | 300.0 mg/ml |
| 3. Isopropyl Alcohol | 300.0 mg/ml |
| 4. Carbomer 940 | 15.0 mg/ml |
| 5. Sodium Hydroxide (q.s. to adjust pH) | — |
| 6. Titanium Droxide | 5.0 mg/ml |
| 7. Water q.s. ad to | 1.0 g |

Combine the ingredients using standard techniques.

| Sterile Solution for Injection: | Concentration |
|---|---|
| 1. Alpha interferon | $10^7$ I.U. |
| 2. Sodium phosphate monobasic | 0.55 mg/ml |
| 3. Sodium phosphate Dibasic | 2.27 mg/ml |
| 4. Glycine | 20 mg/ml |
| 5. Human Serum Albumin | 1.0 mg/ml |
| 6. Purified Distilled Water | 1.0 ml |

Combine the ingredients using standard techniques.

Compositions combining Cycladrine and Alpha Interferon:

| Gel: | Concentration |
|---|---|
| 1. Cycladrine | 25 mg |
| 2. Alpha interferon | $10^6$ I.U. |
| 3. Poloxamer 407 | 200.0 mg/g |
| 4. Monobasic sodium phosphate | 0.13 mg/g |
| 5. Dibasic sodium phosphate | 0.57 mg/g |
| 6. Water q.s. ad to | 1.0 g |

Combine the ingredients using standard techniques.

| Ointment: | Concentration |
|---|---|
| 1. Cycladrine | 20 mg |

| Ointment: | Concentration |
| --- | --- |
| 2. Alpha interferon | $10^6$ I.U. |
| 3. Propylene glycol, U.S.P. | 100.0 mg/g |
| 4. Propylene glycol stearate | 20.0 mg/g |
| 5. White Petrolatum, U.S.P q.s. ad to | 1.0 g |

Combine the ingredients using standard techniques.

Since the cyclaradine is preferably administered orally and the interferon is preferably administered topically or parenterally, the invention also contemplates combining separate pharmaceutical compositions in kit form: that is, combining two separate units, i.e., an oral cyclaradine pharmaceutical composition and a topical or parenteral interferon pharmaceutical composition, in a single package.

We claim:

1. A pharmaceutical composition comprising an antiviral effective amount of a combination of (+)-cyclaradine or an equivalent amount of the 5'-methoxyacetate ester or 5'-ethoxypropionate ester, or a pharmaceutically acceptable salt thereof, and interferon in a pharmaceutically acceptable carrier.

2. A composition of claim 1 wherein the interferon is natural or recombinant alpha interferon.

3. A composition of claim 2 wherein the alpha interferon is alpha-2 interferon.

4. A composition of claim 1 in a form suitable for topical administration.

5. A composition of claim 4 comprising 10–100 mg cyclaradine and $5 \times 10^5$ to $10^7$ I.U. interferon/g of composition.

6. An composition of claim 1 in a form suitable for oral administration.

7. A composition of claim 1 in a form suitable for parenteral administration.

8. A composition of claim 7 comprising 50 to 200 mg cyclaradine and $2.5 \times 10^4$ to $5 \times 10^7$ I.U. interferon/ml.

9. A method of treating Herpes simplex virus wherein a composition of claim 1 is administered to a human in need of such treatment.

10. A method of treating Herpes simplex virus wherein a composition of claim 5 is administered to a human in need of such treatment.

11. A method of treating Herpes simplex virus wherein a composition of claim 6 is administered to a human in need of such treatment.

12. A method of treating Herpes simplex virus wherein a composition of claim 8 is administered to a human in need of such treatment.

13. A method of treatment of Herpes simplex virus, wherein a combination of cyclaradine or a lower alkoxyalkanoate ester thereof and interferon effective in treating Herpes simplex is administered to a human in need of such treatment.

14. The method of claim 13 wherein cyclaradine or a lower alkoxyalkanoate ester thereof is administered 1 to 5 times daily and interferon is administered 1 to 4 times daily.

15. The method of claim 13 wherein cyclaradine or a lower alkoxyalkanoate ester thereof is administered 3 to 4 times daily and interferon is administered 1 to 2 times daily.

16. The method of claim 13 wherein cyclaradine or a lower alkoxyalkanoate ester thereof is administered orally in a dosage range of 1 to 100 mg/kg body weight per day and interferon is administered topically in a dosage range of $10^5$ to $10^8$ I.U. per day.

17. The method of claim 13 wherein the combination is administered up to twenty four hours after exposure to herpes simplex virus.

18. A kit comprising in separate containers in a single package (1) a pharmaceutical composition comprising (+)-cyclaradine or an equivalent amount of the 5'-methoxyacetate or 5'-ethoxypropionate ester, or a pharmaceutically acceptable salt thereof; and (2) a pharmaceutical composition comprising interferon, each component being present in an amount sufficient to provide an effective amount of the combination for the treatment of herpes simplex virus.

* * * * *